(12) United States Patent
Honda (10) Patent No.: US 10,561,429 B2
(45) Date of Patent: Feb. 18, 2020

(54) CALCULUS REMOVING DEVICE

(71) Applicant: TERUMO KABUSHIKI KAISHA, Shibuya-ku, Tokyo (JP)

(72) Inventor: Kei Honda, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 1181 days.

(21) Appl. No.: 14/858,707

(22) Filed: Sep. 18, 2015

(65) Prior Publication Data

US 2016/0081703 A1    Mar. 24, 2016

(30) Foreign Application Priority Data

Sep. 19, 2014  (JP) ................................. 2014-191794

(51) Int. Cl.
  *A61B 17/221*  (2006.01)
(52) U.S. Cl.
  CPC .................. *A61B 17/221* (2013.01)
(58) Field of Classification Search
  CPC ........ A61B 17/32056; A61B 17/32002; A61B 17/22031; A61B 2017/00685; A61B 2017/22037; A61B 2017/221
  See application file for complete search history.

(56) References Cited

U.S. PATENT DOCUMENTS

| 5,591,187 A | 1/1997 | Dekel |
| 6,066,153 A | 5/2000 | Lev |
| 2011/0087257 A1 | 4/2011 | To et al. |
| 2011/0152920 A1* | 6/2011 | Eckhouse ............ A61B 17/221 606/200 |
| 2015/0351784 A1* | 12/2015 | Dao ................. A61B 17/22031 606/128 |

FOREIGN PATENT DOCUMENTS

| JP | H02-071509 U | 5/1990 |
| JP | 2001-512355 A | 8/2001 |
| JP | 2012-522604 A | 9/2012 |
| WO | WO 98/36694 A1 | 8/1998 |

OTHER PUBLICATIONS

Office Action (Notification of Reasons for Refusal) dated May 15, 2018, by the Japanese Patent Office in corresponding Japanese Patent Application No. 2014-191794, and an English Translation of the Office Action. (7 pages).

* cited by examiner

*Primary Examiner* — Diane D Yabut
(74) *Attorney, Agent, or Firm* — Buchanan Ingersoll & Rooney PC (57) ABSTRACT

A calculus removing device includes a cylinder, a screw, and a hand-operated unit. The cylinder includes a storage portion configured to store calculi and broken calculus pieces, and an opening communicating with the storage portion. The screw is helically-shaped, is arranged in the storage portion and is configured to move the calculi to a proximal end of the cylinder while drawing the calculi into the storage portion thereof via the opening in association with the rotation of the cylinder about an axial line along a longitudinal direction of the cylinder. The hand-operated unit includes an operating member for rotating the screw.

17 Claims, 7 Drawing Sheets

CALCULUS REMOVING DEVICE

CROSS-REFERENCES TO RELATED APPLICATIONS

This application claims priority based on Japanese Application No. 2014-191794 filed on Sep. 19, 2014, the entire content of which is incorporated herein by reference.

TECHNICAL FIELD

The present invention generally relates to a calculus removing device.

BACKGROUND DISCUSSION

Urinary stones include stones existing in a urinary tract such as a kidney, a ureter, a bladder, a urethra and the like, and a calculus generated in a kidney or in a ureter is referred to as an upper urinary stone. In urinary tract stone disease, various symptomatic states are caused by these urinary stones. For example, in the case where a calculus generated in a kidney is moved to a ureter, the calculus damages the ureter and causes a pain or blood in the urine, or the calculus blocks the ureter, so that a transient hydronephrosis state is generated, and hence an acute pain (colic pain) from a lower back to a lateral region may result. In order to alleviate or treat these symptoms, removal of the calculus is effective means.

In the urinary tract stone disease, if effects such as natural stone drainage and a conservative medical treatment cannot be expected, and a surgical positive removal method is performed. Examples of the positive removal method include mainly an Extracorporeal Shock Wave Lithotripsy (ESWL), a transurethral resection of Lithotripsy (TUL or URS), and Percutaneous Nephrolithotripsy (PNL or PCNL). Examples of the TUL include an r-TUL (or r-URS) in which a hard renal pelvis ureter mirror (hereinafter, referred to as a rigid ureteroscope) is used, and an f-TUL (or f-URS) in which a soft renal pelvis ureter mirror (hereinafter, referred to as a soft mirror) is used. In the TUL, a calculus in a ureter or a renal pelvis and renal calyx may be directly reached extracorporeally, transvesically, or ureterily by using a rigid ureteroscopeor a soft mirror so that the calculus may be directly broken or extracted. Therefore, advantages such that damage to a ureter, a kidney, or the like may be suppressed more and a high stone free rate may be realized in comparison with ESWL or PNL are achieved. As an apparatus used in the TUL, an apparatus configured to remove a calculus generated in the ureter or the kidney or a plurality of broken calculus pieces generated after having broken the calculus by a laser to the outside of the body while retaining the same with a wire (basket forceps) is known. An example is disclosed in Japanese Application Publication No. 2001-512355.

The extraction of the stones by using the basket forceps is limited in gripping function of the basket forceps or the size of a ureteral lumen or a ureteral access sheath (guiding catheter), and hence the number of the calculi and the broken calculi pieces which may be removed in one operation is limited in a series of stone extracting operations from a step of gripping the broken calculus pieces to a step of carrying the gripped broken calculus pieces to the outside of the body with the basket forceps. Therefore, in order to remove the calculus, it is necessary to perform an insertion and a retraction of the basket forceps many times between the outside of the body and the position where the calculus exists. Accordingly, a user (operator) bears a heavy burden. In addition, various disadvantages for a patient such that a risk of, for example, developing an infection of a urinary tract after the operation or the like increases, and a burden to a ureter due to ischemia or the like is generated due to a lengthening of an operation time for performing the insertion and the retraction of the basket forceps many times, and a risk of relapse increases because the calculi and the broken calculus pieces cannot be removed within a limited time of operation set for suppressing infection following a surgical procedure occur.

By gripping a plurality of calculi, end surfaces of the calculi and the broken calculus pieces expose from a gap between metallic wires which constitute the basket forceps. Therefore, if an attempt is made to remove the plurality of calculi and the broken calculus pieces to the outside of the body at once, inner walls or the like of the kidney and the ureter may become damaged, or an end surface of an opening of a ureteral access sheath on a distal side and exposed portions of the calculi and the broken calculus pieces fit and hence cannot be pulled out to the outside of the body.

SUMMARY

The inventive calculus removing device disclosed here is configured to remove a plurality of calculi and broken calculus pieces reliably to the outside of the body.

A calculus removing device includes: a collecting portion including a storage portion configured to store calculi, and an opening communicating with the storage portion; a helical rotatable portion arranged in the storage portion and configured to move the calculi to a proximal end of the collecting portion while drawing the calculi into the storage portion via the opening in association with a rotation of the helical rotatable portion about an axial center line extending along a longitudinal direction of the rotatable portion; and a hand-operated unit provided with an operating member for rotating the rotatable portion.

The rotatable portion includes a helical surface formed by being wound at cyclic intervals.

The rotatable portion is configured in such a manner that the intervals between adjacent helical surfaces are variable.

The calculus removing device may further include an adjusting member provided adjacent to the rotatable portion in an axial direction extending from the proximal side of the storage portion toward the opening side, and configured to vary the intervals between the adjacent helical surfaces by a back and forth movement along the axial direction.

The rotatable portion may rotate within the storage portion.

The rotatable portion may be integral with the storage portion and rotate with the collecting portion.

The calculus removing device may further include a retrieving member including a communicating port communicating with the collecting portion and a retrieving portion configured to store the calculi moving from the opening side to the proximal side of the storage portion via the communicating port.

The retrieving member may be demountably mounted on the collecting portion.

The collecting portion includes a first storage portion configured to store the calculus, and a second storage portion configured to store the first storage portion so as to be mountable and demountable and coupled to the operating member.

According to the inventive calculus removing device disclosed here, since calculi and broken calculus pieces can be retained sufficiently by the helical rotating portion configured to move the calculi and the broken calculus pieces drawn out in association with the rotation toward the proximal side of the collecting portion, the calculi and the broken calculus pieces can be retained reliably and removed out of the body irrespective of the number and the size. Since the calculi and the broken calculus pieces are retained in the storage portion, the calculi and the broken calculus pieces may be removed safely and reliably to the outside of the body without causing the exposed end surfaces of the calculi and the broken calculus pieces to damage on a living tissue such as an inner wall or the like of the kidney or the ureter or to be caught when being pulled into the ureteral access sheath.

The rotating portion may be significantly simplified by configuring the rotating portion with the helical surface formed by being wound at cyclic intervals, and the calculi and the broken calculus pieces drawn out in association with the rotation may be reliably moved.

The intervals between the adjacent helical surfaces are set arbitrarily or as desired in accordance with the size and the shape of the calculi and the broken calculus pieces to be removed by varying the intervals between the adjacent helical surfaces of the rotating portion, so that the calculi and the broken calculus pieces can be drawn out further effectively.

The intervals between the adjacent helical surfaces of the rotating portion may be varied further reliably by the adjusting member which varies the intervals between the helical surfaces.

Since the rotating portion rotates within the storage portion, the rotating portion is allowed to perform a rotating action reliably without affecting the interior of the living body which is in contact with the outer peripheral surface of the storage portion.

Because the rotating portion rotates with the collecting portion configured integrally therewith, the structure is further simplified, and the rotating portion is allowed to perform the rotating action further reliably.

Since the calculi and the broken calculus pieces collected in the collecting portion may be retrieved by the retrieving member, the calculi and the broken calculus pieces exceeding the capacity of the collecting portion may be removed.

By removable mounting the retrieving member to the collecting portion, in the case where a pathological examination is performed with respect to the calculi and broken calculus pieces and the calculi and broken calculus pieces are discarded, the handling may be performed more simply.

Since the collecting portion includes the first storage portion configured to store the calculi and broken calculus pieces and the second storage portion configured to store the first storage portion so as to be mountable and demountable and coupled to the operating member, the first storage portion filled with the calculi and broken calculus pieces may be demounted from the second storage portion and a new first storage portion may be mounted in the second storage portion. Therefore, in the case where a pathological examination is performed with respect to the calculi and broken calculus pieces and the calculi and broken calculus pieces are discarded, the handling may be performed simply.

According to another aspect, a calculus removing device comprises: a calculus collection housing configured to be introduced into a living body, wherein the calculus collection housing possesses a proximal end, and an interior configured to receive and store calculus collected from the living body, and wherein the calculus collection housing includes an opening which opens into the interior of the calculus collection housing and through which the calculus in the living body is introduced into the interior of the calculus collection housing; a rotatable portion possessing a helically extending periphery, with the helically extending periphery being located in the interior of the calculus collection housing portion and the rotatable portion being rotatable about an axial center line of the rotatable portion; and an operating member operatively connected to the rotatable portion so that operation of the operating member rotates the rotatable portion, including the helically extending periphery, so that the rotating helically extending periphery draws the calculus through the opening and into the interior of the calculus collection housing and moves the calculus which has been drawn into the interior of the calculus collection housing toward the proximal end of the calculus collection housing.

Another aspect of the disclosure involves a method comprising: introducing a calculus collection housing into a living body, with the calculus collection housing possessing an interior and including an opening which opens into the interior of the calculus collection housing; moving the calculus collection housing in the living body to position the opening of the calculus collection housing adjacent calculus in the living body; rotating a helically extending portion in the interior of the calculus collection housing when the opening of the calculus collection housing is adjacent the calculus in the living body so that the rotating helically extending portion draws the calculus through the opening and into the interior of the calculus collection housing; and continuing to rotate the helically extending portion to move the calculus which has been drawn through the opening and into the interior of the calculus collection housing toward the proximal end of the calculus collection housing.

DETAILED DESCRIPTION

Figure 1A:
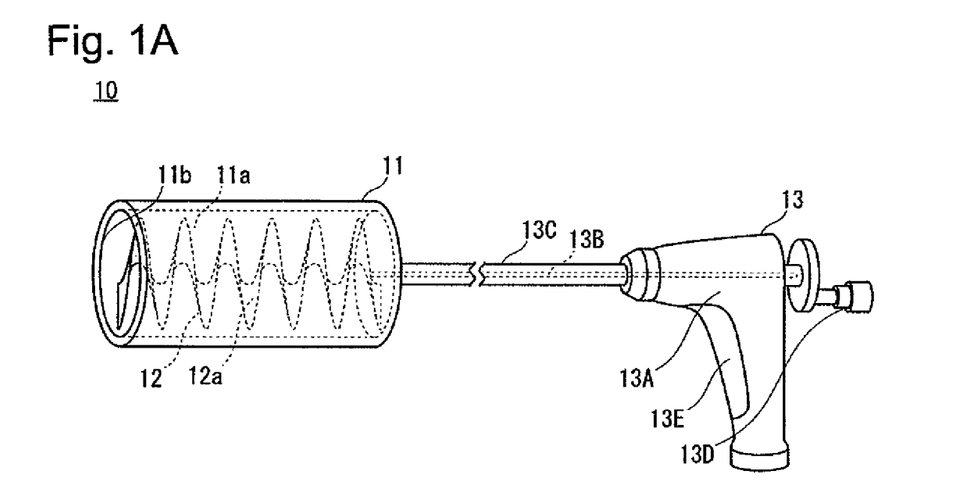
FIG. 1A is a perspective view of a calculus removing device of a first embodiment illustrating a state before a rotatable portion in a storage portion of a collecting portion is rotated.
Figure 1B:
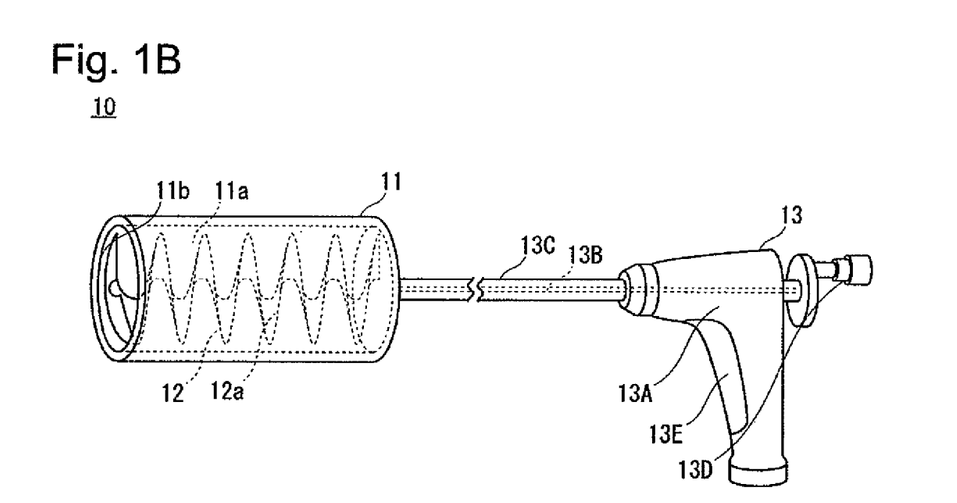
FIG. 1B is a perspective view of the calculus removing device of the first embodiment illustrating a state in which the rotatable portion is rotated by 180 degrees.

Embodiments of the calculus removing device representing examples of the inventive calculus removing device disclosed here will be described with reference to the drawings. Dimensional ratios of the drawings are exaggerated for convenience of description and may be different from actual ratios. For example, in a calculus removing device 10 illustrated in FIG. 1 or the like, the sizes of a cylinder 11 and a screw 12 are significantly exaggerated in comparison with a hand-operated unit 13. The size of the calculus removing device 10 may be imagined by referring to FIG. 3. The proximal side or proximal end corresponds to the side or end of a user (operator) and the distal side or distal end corresponds to the side or end of the living body where the calculus removing device 10 or the like is introduced.

First Embodiment

The calculus removing device 10 of a first embodiment will be described.

A configuration of the calculus removing device 10 will be described with reference to FIGS. 1A and 1B.

FIGS. 1A and 1B are perspective views of the calculus removing device 10 of the first embodiment. FIG. 1A illustrates a state before the screw 12 in a storage portion 11a of the cylinder 11 is rotated. FIG. 1B illustrates a state in which the screw 12 is rotated by 180 degrees.

The calculus removing device 10 collects a calculus K and broken calculus pieces generated in an ureter 230 or the like and removes the calculi K and the broken calculus pieces to the outside of the body and/or into a bladder in a state of being retained by being twined by the screw 12. The calculus K and the broken calculus pieces exist in a urinary tract. The broken calculus pieces include the calculus K existing in the urinary tract, in a form of being broken up by, for example, a laser breaking apparatus to relatively small pieces.

In the following description, the calculi K include the broken calculus pieces.

The calculus removing device 10 includes a collecting portion (which corresponds to the cylinder 11), a rotatable portion (which corresponds to the screw 12) and the hand-operated unit 13.

The cylinder 11 is a calculus collection housing that collects the calculi K in the storage portion 11a of the cylinder 11. The cylinder 11 is provided with the storage portion 11a and an opening 11b. The storage portion 11a possesses a cylindrical shape having a predetermined capacity for storing the calculi K and is provided with the opening 11b at one end of the cylinder/storage portion and a blocked or closed proximal side (proximal end), which corresponds to the other end. The dimensions such as the outer size of outer diameter or the like of the cylinder 11 may be modified as needed as long as it can be introduced into a living body organ, which is an object, such as the ureter 230 or the like. The storage portion 11a is formed of, for example, a resin having flexibility, and may be deformable so as to match the shape of the ureter 230 or the like. The storage portion 11a is formed of a material which is transparent in a visible light region, so that a state of storage of the calculi K is visible from the outside. The cylinder 11 may include or be coated with a radiographic contrast agent so as to allow imaging from the outside by using an X-ray for confirmation of the position within the living body. The opening 11b opens into and is in communication with the storage portion 11a. The calculi K are stored in the storage portion 11a via the opening 11b. The cylinder 11 may have a configuration in which the position cylinder in the living body may be confirmed by being viewed fluoroscopically from the outside in a state of being filled with a radiographic contrast agent.

The screw 12 moves the calculi K to the proximal end of the storage space while drawing the calculi K into the cylinder 11. The screw 12 moves the calculi K toward the proximal end of the cylinder 11 while drawing the calculi K into the storage portion 11a via the opening 11b in association with the rotation of the cylinder 11 about an axial center line along the longitudinal direction of the cylinder 11. The screw 12 includes or defines a helical surface 12a formed by an outer surface that is wound at cyclic intervals. That is, the screw 12 possesses a helically extending periphery. The screw 12 is arranged rotatably in the interior of the storage portion 11a of the cylinder 11. The intervals between the axially adjacent helical surfaces 12a (or surface portions) are not specifically limited. The screw 12 is possesses a hollow shape having a through hole penetrating through the center portion of the screw 12 in an axial direction. The screw 12 is expandable as a whole and has a resiliency. The rotatable portion is not limited to a configuration in which the helical surface 12a is formed continuously. A configuration is possible in which the helical surface is formed intermittently in a frame shape and a configuration is also possible in which the helical surface is formed in a mesh-shape.

The hand-operated unit 13 allows a user (operator) to rotate the screw 12 or perform an operation for adjusting a position of the cylinder 11 in which the screw 12 is arranged. The hand-operated unit 13 includes an operating member 13D for rotating the screw 12 relative to the cylinder 11. The hand-operated unit 13 is provided with a retaining member 13A, a rotating member 13B, a protective member 13C, the operating member 13D, and a gripping member 13E.

The retaining member 13A corresponds to a main body of the hand-operated unit 13. The retaining member 13A is cylindrically-shaped, and the protective member 13C is coupled at one of its ends to the cylinder 11 along the axial direction of the cylinder 11 and is coupled at the other of its ends to the operating member 13D. The retaining member 13A allows insertion of the rotating member 13B through the retaining member 13A so as to connect the protective member 13C and the operating member 13D. The gripping member 13E is connected to a lower portion of the retaining member 13A. The rotating member 13B is configured to transmit the rotary action of the operating member 13D to the screw 12. The hand-operated unit 13 is thus operatively connected to the screw 12 so that operation of the hand-operated unit 13 (the rotating member 13D) is transmitted to and rotates the screw 12. The rotating member 13B has flexibility, and possesses a columnar shape. The rotating member 13B is formed of a wire, for example, which can be deformed so as to match the shape of the ureter 230 or the like or the movement of a flexible ureteroscope 100. The proximal end of the rotating member 13B is coupled to the operating member 13D, and the distal end of the rotating member 13B is coupled to the screw 12.

The protective member 13C is configured to protect the rotating member 13B while storing or enclosing the rotating member 13B in the interior of the protective member 13C in a rotatable manner. The protective member 13C has flexibility and possesses a cylindrical shape. The protective member 13C is deformable so as to match the shape of the ureter 230 or the like or the movement of the flexible ureteroscope 100. The proximal end of the protective member 13C is removably coupled to the retaining member 13A so as to be demountably mountable by fitting or press fitting. The operating member 13D is configured to operate the rotation of the screw 12. The operating member 13D is formed, for example, of a handle and is coupled to the rotating member 13B. As illustrated in FIG. 1B, if the user (operator) rotates the operating member 13D, the rotating member 13B rotates correspondingly, so that the screw 12 coupled to the rotating member 13B rotates. The gripping member 13E is a member gripped by the user (operator). The gripping member 13E is connected to and extends downwardly from a lower portion of the retaining member 13A.

A manner of using the calculus removing device 10 will be described with reference to FIG. 2 to FIG. 4C.

Figure 2:
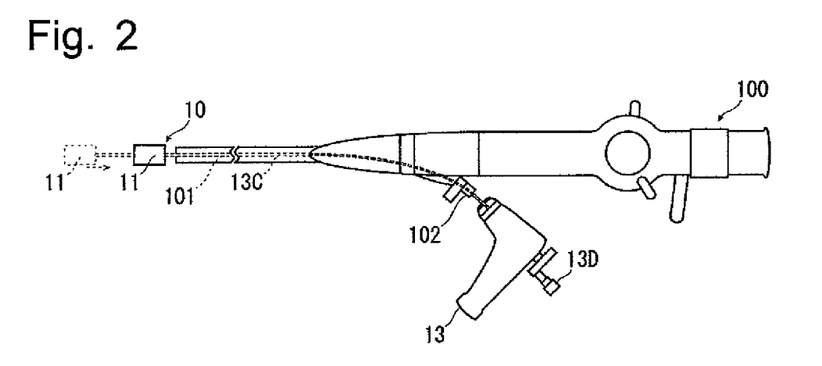
FIG. 2 is a schematic drawing illustrating a state in which the calculus removing device is mounted on a flexible ureteroscope
Figure 3:
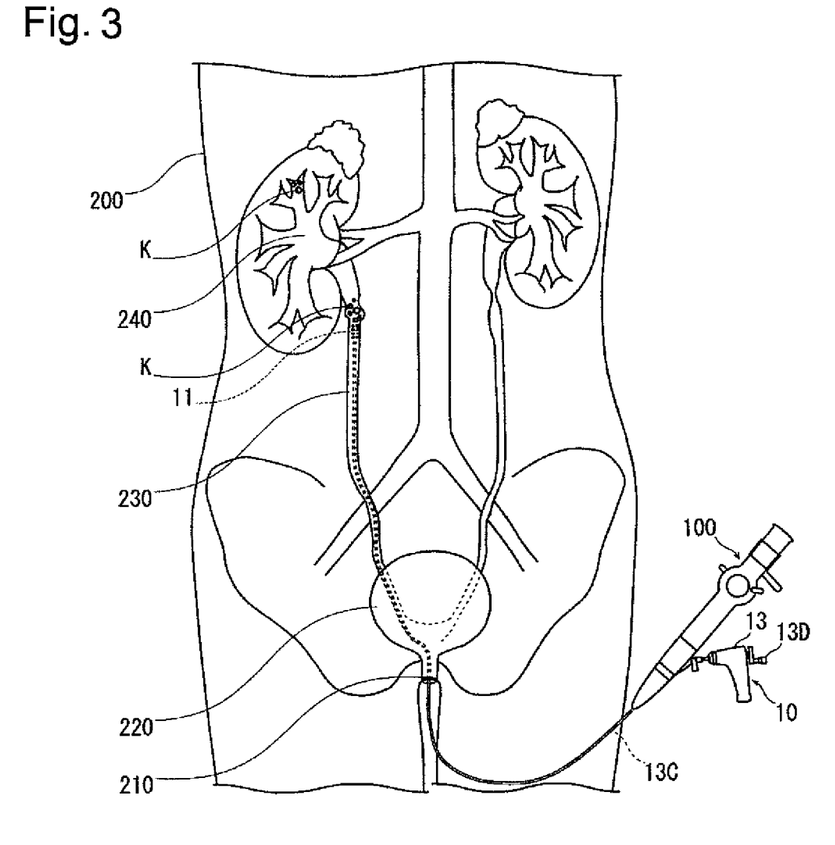
FIG. 3 is a schematic drawing illustrating a state in which the flexible ureteroscope on which the calculus removing device is mounted is introduced into a ureter of a patient.
Figure 4A:
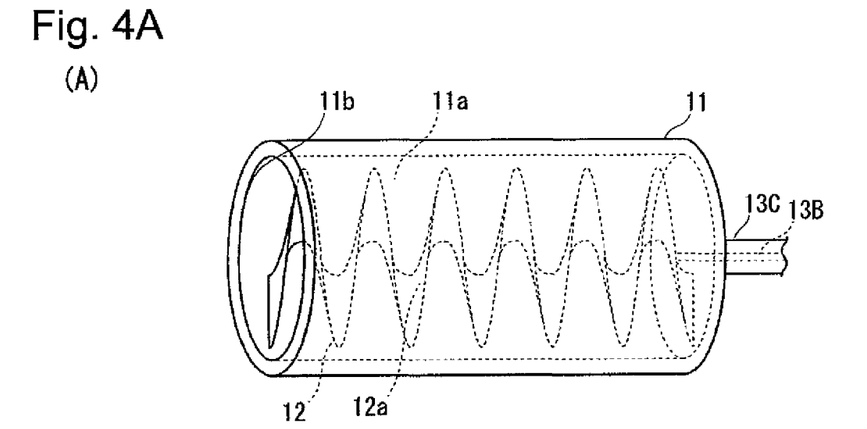
FIG. 4A is a schematic drawing of a state in which calculi and broken calculus pieces are collected in the collecting portion of the calculus removing device illustrating the storage portion of the collecting portion.
Figure 4B:
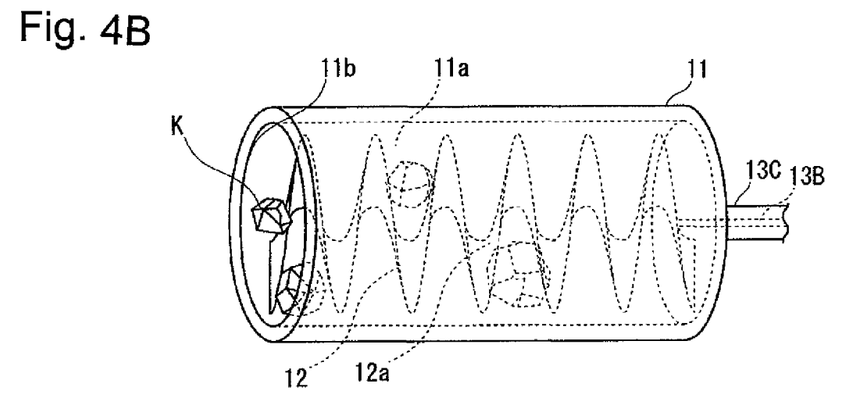
FIG. 4B is a schematic drawing of a state in which the calculi and broken calculus pieces are collected in the collecting portion of the calculus removing device illustrating the plurality of calculi and broken calculus pieces are drawn into the storage portion of the collecting portion while rotating the rotatable portion.
Figure 4C:
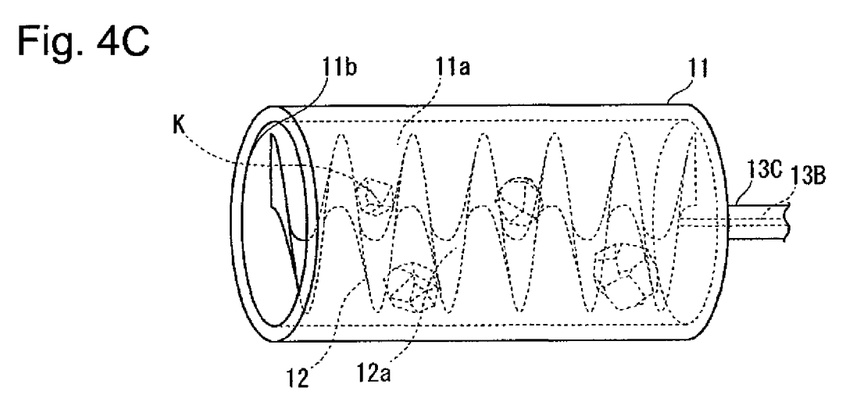
FIG. 4C is a schematic drawing of a state in which the calculi and broken calculus pieces are collected in the collecting portion of the calculus removing device illustrating a state in which the plurality of calculi and broken calculus pieces are drawn into the storage portion of the collecting portion while rotating the rotatable portion and moved to a proximal side.

FIG. 2 schematically illustrates a state in which the calculus removing device 10 is mounted on the flexible ureteroscope 100. FIG. 3 schematically illustrates a state in which the flexible ureteroscope 100 on which the calculus removing device 10 is mounted is introduced into the ureter 230 of a patient 200. FIGS. 4A to 4C schematically illustrate a state in which the calculi K are collected in the cylinder 11 of the calculus removing device 10. FIG. 4A illustrates the storage portion 11a of the cylinder 11. FIG. 4B illustrates a state in which the plurality of calculi K are drawn into the storage portion 11a of the cylinder 11 while rotating the screw 12. FIG. 4C illustrates a state in which the plurality of calculi K are drawn into the storage portion 11a of the cylinder 11 and moved to the proximal end of the storage space while rotating the screw 12.

A cystoscope, which is generally used in the urinary system is used for the patient 200 illustrated in FIG. 3, and a guide wire widely known in a medical field is introduced into the ureter 230 or a renal pelvis and renal calyx 240 via a urethra 210 and a bladder 220. Subsequently, a rigid ureteroscope is inserted to monitor an inner wall of the ureter 230 and the calculi K in the ureter 230. At this time, the calculi K may be removed by using a basket forceps together with the rigid ureteroscope. The calculi K which are relatively large and are difficult to remove may be broken into relatively small pieces using a breaking apparatus such as a Ho: YAG laser or the like together with the rigid ureteroscope. The created broken calculus pieces may then be removed using the basket forceps. Subsequently, the rigid ureteroscope is removed from the living body.

Subsequently, a ureteral access sheath is introduced into the ureter 230 or the renal pelvis and renal calyx 240 via the urethra 210 and the bladder 220 via the guide wire.

The flexible ureteroscope 100 is inserted via the ureteral access sheath to monitor the calculi K. At this time, the guide wire may be removed. In the case where the calculi have a relatively large size which makes the calculi K difficult to pass through the ureteral access sheath, the calculi K are broken into a relatively small size using the breaking apparatus such as Ho: YAG laser or the like together with the flexible ureteroscope 100.

Subsequently, the calculus removing device 10 and the flexible ureteroscope 100 are assembled. Specifically, as illustrated in FIG. 2, from a state in which the retaining member 13A, the rotating member 13B and the protective member 13C of the hand-operated unit 13 of the calculus removing device 10 are separated, the rotating member 13B and the protective member 13C are introduced into a working channel 101 of the flexible ureteroscope 100 from a distal end of the flexible ureteroscope 100 and are led to cause the proximal ends of the rotating member 13B and the protective member 13C to be led out from a port 102, the proximal side of the protective member 13C is fitted into the retaining member 13A of the hand-operated unit 13, and the proximal side of the rotating member 13B is fitted into and mounted on the operating member 13D of the hand-operated unit 13.

As illustrated in FIG. 3, the calculi K are collected in the cylinder 11 using the calculus removing device 10 after the flexible ureteroscope1 00 provided with the calculus removing device 10 has reached, via the urethra 210 and the bladder 220 of the patient 200, a portion in the ureter 230 where the calculi K exist.

Specifically, the storage portion 11a of the cylinder 11 illustrated in FIG. 4A is pressed against the calculi K in the ureter 230 illustrated in FIG. 3 from the side of the hand-operated unit 13. In a state in which the calculi K are pressed by the storage portion 11a, as shown in FIG. 4B to FIG. 4C, the screw 12 is rotated to move the plurality of calculi K in the proximal direction toward the proximal end of the cylinder 11 while drawing the calculi K into the storage portion 11a in sequence. The calculus removing device 10 in which the calculus K is collected into the cylinder 11 is then moved to the outside of the living body, and the calculi K are removed to the outside of the cylinder 11 from the opening 11b. To accomplish this, the operating member 13D is rotated to an opposite direction from that in the case where the calculi K are drawn into the storage portion 11a, and the screw 12 is rotated in conjunction with the operation of the operating member 13D in the opposite direction, whereby the calculi K stored in the storage portion 11a are moved to the distal end of the cylinder 11 and are retrieved.

A series of steps described above are repeated until intended calculi K are removed completely. A portion where the calculi K are removed from the storage portion 11a is outside the living body, in addition, calculi K can be removed from the storage portion 11a within the bladder as necessary. In addition, for the purpose of changing the position of the calculi (repositioning), the calculi K may be drawn into the storage portion 11a in a renal calyx within the renal pelvis, moved and then released in another renal calyx.

The calculus removing device 10 may be used together with the rigid ureteroscope. In other words, in the operation including the monitoring with the rigid ureteroscope, breakup of the stones, and extraction of the stone to be performed prior to the operation of extraction of the stone with the flexible ureteroscope 100, the calculus removing device 10 may be used instead of the basket forceps.

Subsequently, the guide wire is introduced into the ureter 230 or the renal pelvis and renal calyx 240 via the urethra 210 and the bladder 220. In addition, an indwelling ureter stent for the upper ureter is indwelled so as to cover the guide wire, and then the guide wire is pulled out. The ureter stent is used for preventing a transient blockage of the ureter or the like after the operation. The ureter stent is removed after a predetermined number of days have passed or elapsed.

The technique described with reference to FIG. 2 to FIGS. 4A to 4C is mainly as follows. The technique generally involves a method of collecting the calculi K by introducing a device into the living body of the patient 200 and then later removing the device to outside of the body. More specifically, the method involves preparing the calculus removing device 10 configured to move the calculi K to the proximal end of the cylinder 11 while drawing the calculi K into the storage portion 11a by rotating the screw 12, introducing the calculus removing device 10 mounted on the flexible ureteroscope 100 into the living body, and removing the calculi K stored in the storage portion 11a to the outside of the body via the opening 11b of the cylinder 11.

As described above, according to the calculus removing device 10 of the first embodiment, with the helical screw 12 configured to move the calculi K to the proximal end of the cylinder 11 while drawing the calculi K into the storage portion 11a via the opening 11b in association with the rotation about the center axis extending along the longitudinal direction of the cylinder 11, the calculi K may be retained sufficiently by the helical screw 12 configured to draw-in the calculi K, in association with the rotation of the screw, to the proximal end of the cylinder 11, so that the calculi K may be retained reliably and removed to the outside of the body.

In addition, since the calculus removing device 10 is configured to store the plurality of calculi K at once (at the same time) in the storage portion 11a, a removal efficiency of the calculi K may be significantly improved. In other words, by using the calculus removing device 10, the time required for removing the plurality of calculi K may be significantly reduced, and a larger number of the calculi K may be removed within a certain period of time. Even though the upper limit of the time for the surgical operation is limited, for example, for preventing an infection of the urinary tract after the surgical operation, a larger number of the calculi K may be removed to the outside of the body, so that the stone free rate may be improved.

In addition, since the calculus removing device 10 is capable of storing the plurality of calculi K having different sizes in the storage portion 11a, the calculi K having relatively small sizes and the large calculi K can be removed at once (at the same time).

In addition, since the calculus removing device 10 is capable of storing the calculi K in the storage portion 11a, the calculi K removed from the ureter 230 or the like may be removed to the outside of the body without coming into contact with and causing rupture of an inner wall of the ureter 230 or the bladder 220.

In addition, since the calculus removing device 10 is capable of storing the calculi K in the storage portion 11a, the calculi K removed from the ureter 230 or the like may be removed to the outside of the body without engaging the opening of the ureteral access sheath and making the ureteral access sheath difficult to be pulled out.

The screw 12 may be significantly simplified by configuring the screw 12 with the helical surface 12a formed by being wound at cyclic intervals, and the calculi K drawn out in association with the rotation of the screw/helical surface may be reliably moved.

Since the screw 12 rotates within the storage portion 11a, the rotary action of the screw 12 is ensured without affecting the interior of the living body which is in contact with the outer peripheral surface of the storage portion 11a.

Second Embodiment

A calculus removing device 20 of a second embodiment will be described with reference to FIGS. 5A and 5B. The calculus removing device 20 of this second embodiment is different from the calculus removing device 10 of the first embodiment described above in that the intervals between adjacent helical surfaces 22a of a screw 22 are variable. In the second embodiment, features which are the same as in the first embodiment are identified by common reference numerals, and a detailed description of such features is not repeated.

The configuration of the calculus removing device 20 and a manner of using the calculus removing device 20 will be described with reference to FIGS. 5A and 5B.

Figure 5A:
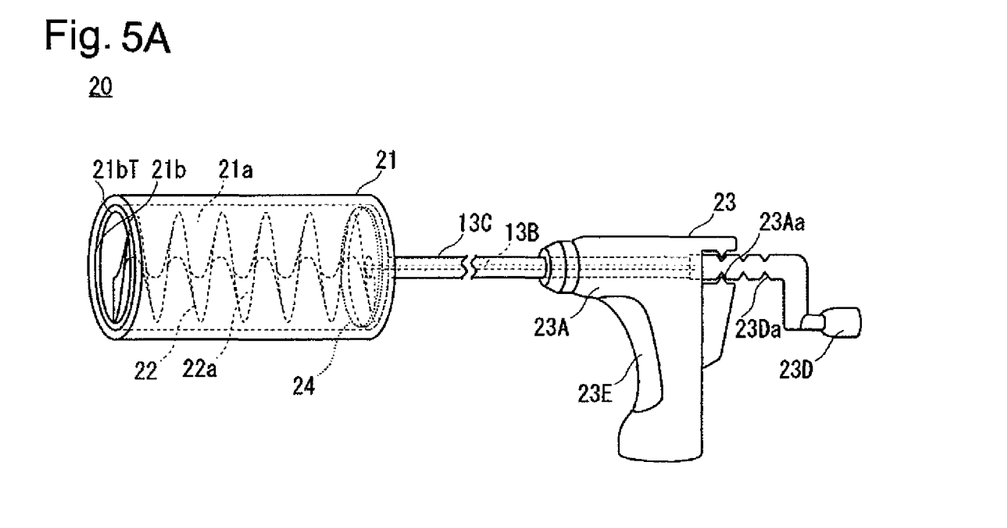
FIG. 5A is a perspective view of a calculus removing device of a second embodiment illustrating a state before a rotatable portion in a storage portion of a collecting portion is adjusted.
Figure 5B:
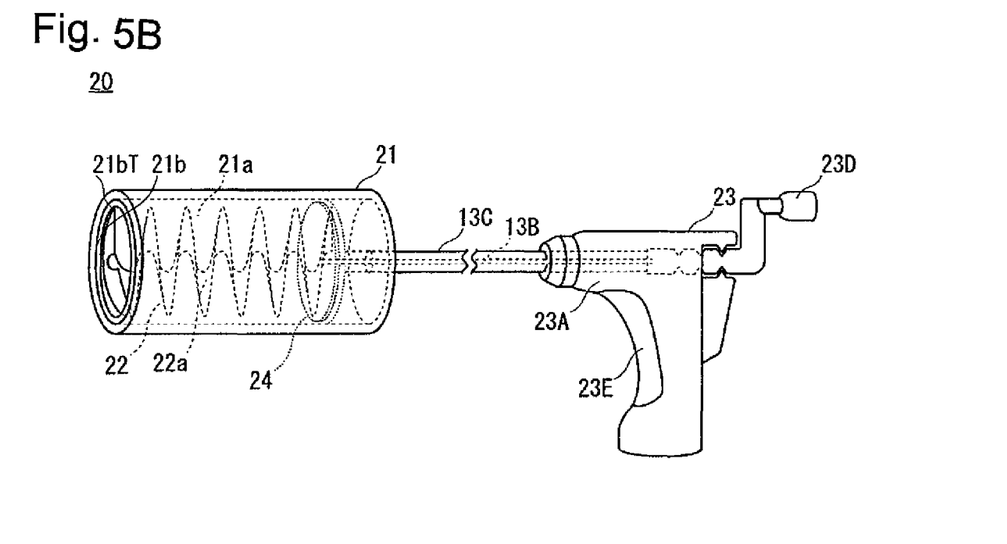
FIG. 5B is a perspective view of the calculus removing device of the second embodiment illustrating a state in which the rotatable portion is pressed by a hand operating unit so that intervals between adjacent helical surfaces are adjusted so as to reduce the intervals therebetween.

FIGS. 5A and 5B are perspective views of the calculus removing device 20 of the second embodiment. FIG. 5A illustrates a state before the screw 22 in a storage portion 21a of a cylinder 21 is adjusted. FIG. 5B illustrates a state in which the screw 22 is pressed by a hand-operated unit 23 to adjust the intervals between the adjacent helical surfaces 22a to reduce.

The screw 22 has the same configuration as the screw 12 except for having flexibility to allow deformation along the axial direction. In other words, the screw 22 is configured to be capable of varying the intervals or axial distance between the adjacent helical surfaces 22a along the axial direction of the cylinder 21. The overall shape or configuration of the screw 22 is the same as the overall shape or configuration of the of the screw 12.

An adjusting member 24 is located adjacent the screw 22 in an axial direction from the proximal end of the storage portion 21a toward the opening 21b and varies the intervals or axial distance between the adjacent helical surfaces 22a by a back and forth movement of the adjusting member 24 along the axial direction. The adjusting member 24 possesses a disc shape, and is rotatably stored in the cylinder 21 on the proximal side of the cylinder 21 or the storage space 21a. A direction of thickness of the adjusting member 24 extends along the axial direction of the cylinder 21. The adjusting member 24 is connected to the proximal end of the screw 22. A distal end of a rotating member 23B of the hand-operated unit 23 is joined to the adjusting member 24.

Part of the distal end of the screw 22 is in contact with a projection 21bT provided at the opening 21b. The projection 21bT is provided, for example, on a circumference of the opening 21b along an inner surface of the circumference, and is configured in such a manner that when the adjusting member 24 is pushed to the distal end (in the distal direction) of the cylinder 21 to reduce the intervals between the adjacent helical surfaces 22a of the screw 22, the screw 22 is prevented from being exposed from the cylinder 21 via the opening 21b, so that the axial deformation of the screw 22 is effectively realized. The distal end portion of the screw 22 and the projection 21bT are not joined to each other, and hence the rotation of the screw 22 in the interior of the cylinder 21 is not impaired.

The more that the operating member 23D of the hand operating unit 23 is introduced into a retaining member 23A, the smaller the intervals (axial distance) between the axially adjacent helical surfaces 22a become. The operating member 23D is provided with a plurality of depressions 23Da on a portion to be introduced into the retaining member 23A along the axial direction. The operating member 23D may be fixed at a position of an arbitrary one of the plurality of depressions 23Da. The depressions 23Da of the operating member 23D fit into a projection 23Aa provided on the retaining member 23A.

As described thus far, according to the calculus removing device 20 of the second embodiment, the screw 22 is configured to be varied in intervals between the adjacent helical surfaces 22a. Therefore, the intervals between the adjacent helical surfaces 22a may be set arbitrarily or at a desired interval/distance in accordance with the size and the shape of the calculi K to be removed, so that the calculi K having desired sizes may be selectively drawn out. In other words, the calculus removing device 20 is capable of removing the calculi K having intended sizes effectively.

With the provision of the adjusting member 24 provided adjacent to the screw 22 in the axial direction from the proximal side of the storage portion 21a toward the opening 21b side, and configured to vary the intervals or axial distance between the adjacent helical surfaces 22a by the back and forth movement along the axial direction, the intervals between the adjacent helical surfaces 22a of the screw 22 may be varied further reliably. In addition, entry of the calculi K into the hand operating unit 23 beyond the adjusting member 24 is prevented.

Third Embodiment

A calculus removing device 30 of a third embodiment will be described with reference to FIGS. 6A and 6B. The calculus removing device 30 of this third embodiment is different from the calculus removing device 10 or 20 of the first embodiment or the second embodiment described above in terms of the configuration by which the cylinder 11 to which a screw 32 is joined is rotated. In the third embodiment, features which are the same as in the first embodiment or the second embodiment are identified by common reference numerals, and a detailed description of such features is not repeated.

The configuration of the calculus removing device 30 and a manner of using the calculus removing device 30 will be described with reference to FIGS. 6A and 6B.

Figure 6A:
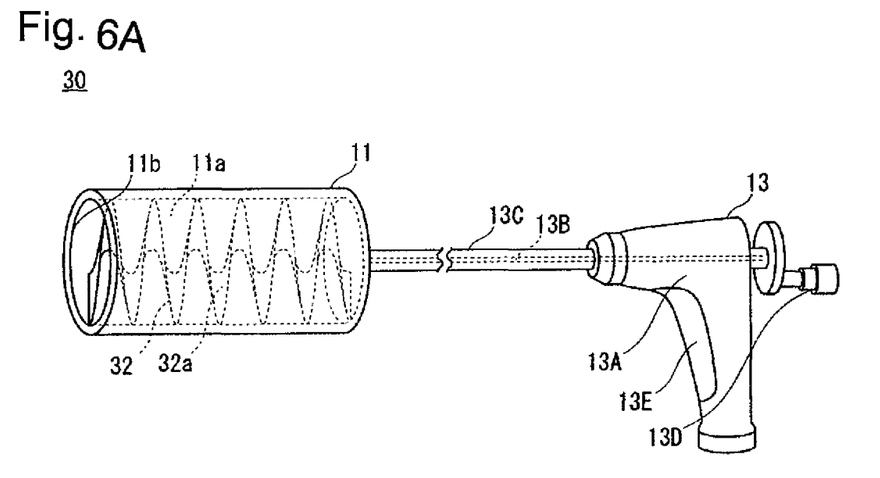
FIG. 6A is a perspective view of a calculus removing device of a third embodiment illustrating a state before a collecting portion is rotated.
Figure 6B:
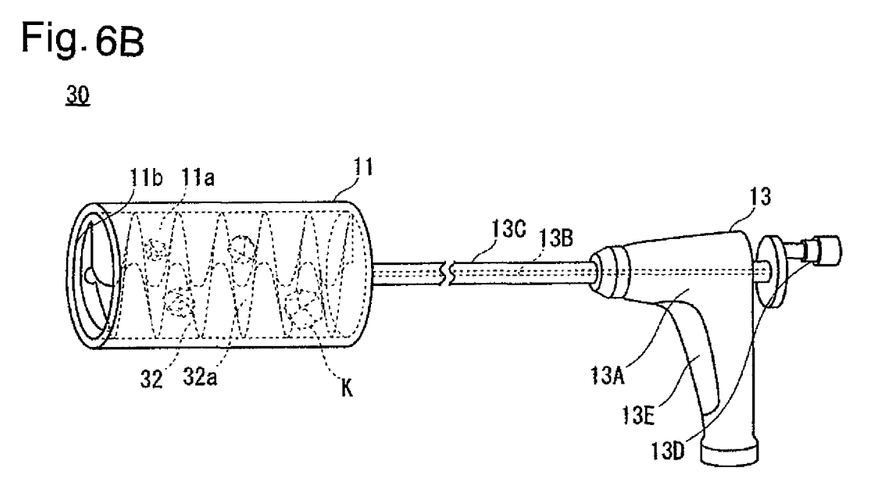
FIG. 6B is a perspective view of the calculus removing device of the third embodiment illustrating a state in which a plurality of calculi and broken calculus pieces are drawn into a storage portion by a rotatable portion while rotating the collecting portion.

FIGS. 6A and 6B are perspective views of the calculus removing device 30 of the third embodiment. FIG. 6A illustrates a state before the cylinder 11 is rotated. FIG. 6B illustrates a state in which the plurality of calculi K are drawn into the storage portion 11a by the screw 32 while rotating the cylinder 11.

The screw 32 has the same configuration as the screw 12 in the first embodiment except that the screw 12 is joined to the inner peripheral surface of the cylinder 11. The screw 32 extends toward the circumferential direction with reference to the axis of rotation , and is, for example, fixedly adhered to the inner peripheral surface of the cylinder 11. A distal end of the rotating member 13B of the hand operating unit 13 is joined to the proximal end of the cylinder 11. When the operating member 13D of the hand operating unit 13 is rotated, the cylinder 11 to which the screw 32 is joined follows and rotates. The hand-operated unit 13 is thus operatively connected to the cylinder 11 and the screw 32 so that operation of the hand-operated unit 13 (the rotating member 13D) is transmitted to and rotates the screw 12 and the cylinder 11.

As described thus far, according to the calculus removing device 30 of the third embodiment, the screw 32 is formed integrally with the storage portion 11a, and rotates together with the cylinder 11, so that the structure is further simplified, and the rotary action of the screw 32 is further ensured.

Fourth Embodiment

A calculus removing device 40 of a fourth embodiment will be described with reference to FIGS. 7A and 7B. The calculus removing device 40 is different from the calculus removing devices 10, 20, and 30 of the first to third embodiments described above in terms of the configuration of the cylinder 41 by which a retrieving pocket 43 configured to retrieve the calculi K is provided in the cylinder 41. In the fourth embodiment, features which are the same as in the first to third embodiments are identified by common reference numerals, and a detailed description of such features is not repeated.

A configuration and how to use the calculus removing device 40 will be described with reference to FIGS. 7A and 7B.

Figure 7A:
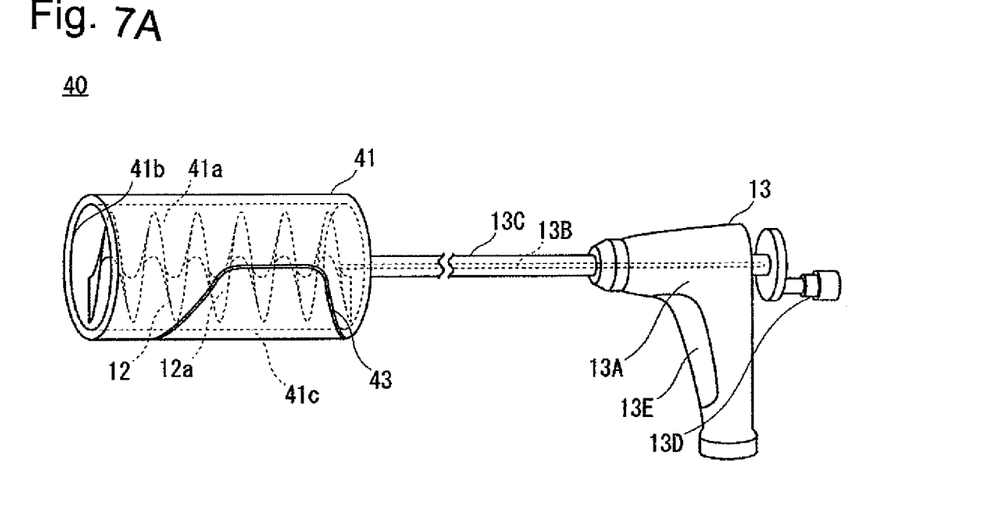
FIG. 7A is a perspective view of a calculus removing device of a fourth embodiment illustrating a state in which a retrieving member is mounted on the outer peripheral surface of a collecting portion.
Figure 7B:
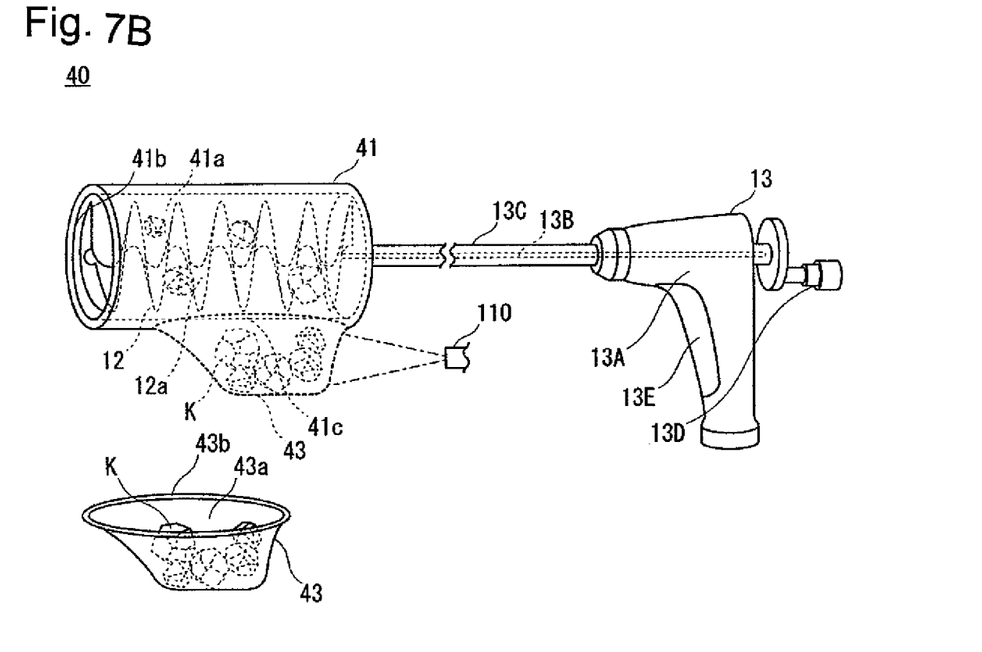
FIG. 7B is a perspective view of the calculus removing device of the fourth embodiment illustrating a state in which the retrieving member which has retrieved a plurality of calculi and broken calculus pieces is demounted from the collecting portion.

FIGS. 7A and 7B are perspective views of the calculus removing device 40 of the fourth embodiment. FIG. 7A illustrates a state in which the retrieving pocket 43 is mounted on an outer peripheral surface of the cylinder 41. FIG. 7B illustrates a state in which the retrieving pocket 43 in which the plurality of calculi K are retrieved is demounted or removed (separate) from the cylinder 41.

The cylinder 41 corresponds to a configuration in which a discharging portion 41c is provided in the cylinder 11. The discharging portion 41c is configured to penetrate through the cylinder from the inner peripheral surface to the outer peripheral surface on the proximal side of the cylinder. The retrieving pocket 43 is mounted on an outer peripheral edge of the discharging portion 41c from the outer peripheral surface side of the cylinder 41.

The retrieving pocket 43 possesses a bag shape provided with a communicating port 43b. The retrieving pocket 43 has flexibility so as to be curved to follow the outer peripheral surface of the cylinder 41 before the retrieval of the calculi K, for example. In other words, the retrieving pocket 43 may be introduced easily into the living body with little interference with the ureter 230. The communicating port 43b of the retrieving pocket 43 is demountably or removably mounted on an outer peripheral edge of the discharging portion 41c of the cylinder 41. A configuration of mounting and demounting (removing) the communicating port 43b of the retrieving pocket 43 and the discharging portion 41c of the cylinder 41 may employ, for example, a so-called tape having sufficient adhesiveness or a hook configured to fit a projection into a depression.

As described above, according to the calculus removing device 40 of the fourth embodiment, since the retrieving pocket 43 including the communicating port 43b communicating with the cylinder 41 and a retrieving portion 43a capable of storing the calculi K moving from an opening 41b side to the proximal side of a storage portion 41a via the communicating port 43b is provided, the calculi K collected in the cylinder 41 can be retrieved and the calculi K exceeding the capacity of the cylinder 41 can be removed. In addition, the retrieving pocket 43 projects from the outer peripheral surface of the cylinder 41 especially in the state in which the calculi K are stored in the retrieving pocket 43, and so confirmation during the surgical operation with a camera 110 is allowed as schematically illustrated in FIG. 7B. The camera 110 is provided at a distal end of the flexible ureteroscope 100, and is provided in the vicinity of an opening of a working channel 101 of the flexible ureteroscope 100.

The retrieving pocket 43 is demountably (removably) mounted on the cylinder 41, so that handling of the calculi K in the case of sending the calculi K to the pathology examination and discarding the calculi K is simplified. In other words, it is not necessary to scrape the calculi K together from a drape and put them in a sample bottle. In addition, in the case where the plurality of calculi K cannot be collected at the same time in the cylinder 41, removal of the calculi K may be continued by replacing only the retrieving pocket 43.

Fifth Embodiment

A calculus removing device 50 of a fifth embodiment will be described with reference to FIGS. 8A and 8B. The calculus removing device 50 of this fifth embodiment is different from the configurations of the calculus removing devices 10, 20, 30, and 40 of the first to fourth embodiments described above in that an inner cylinder 51M as a first storage portion configured to store the calculi K is mountable on and demountable (removable) from an outer cylinder 51N as a second storage portion. In the fifth embodiment, features which are the same as in the first to fourth embodiments are identified by common reference numerals, and a detailed description of such features is not repeated The configuration of the calculus removing device 50 and a manner of using the calculus removing device 50 will be described with reference to FIGS. 8A and 8B.

Figure 8A:
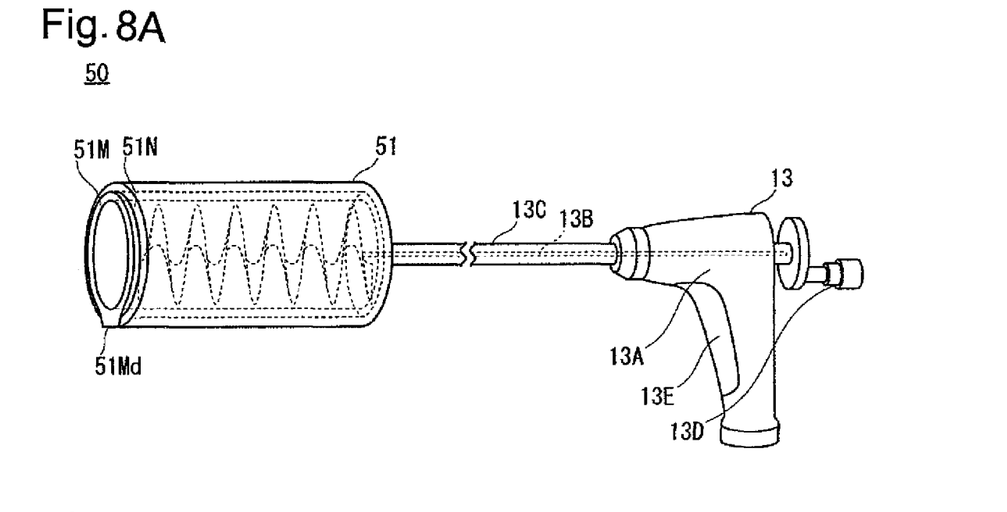
FIG. 8A is a perspective view of a calculus removing device of a fifth embodiment illustrating a collecting portion in a state in which a first storage portion is stored in a second storage portion.
Figure 8B:
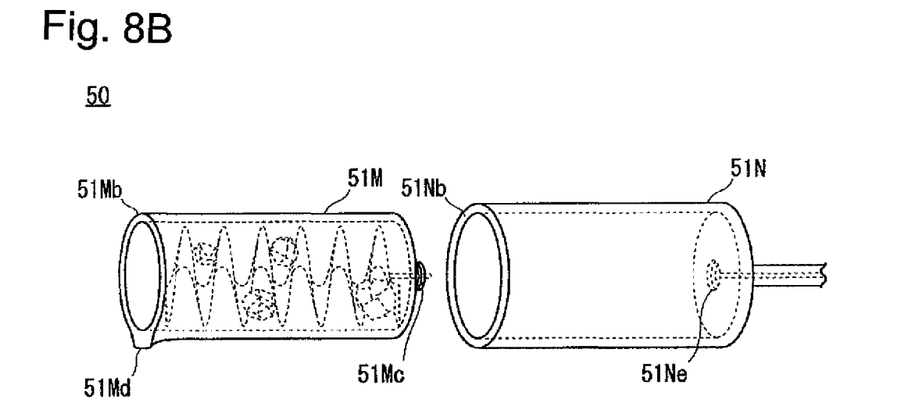
FIG. 8B is a perspective view of the calculus removing device of the fifth embodiment illustrating the collecting portion in a state in which the first storage portion which retains a plurality of calculi and broken calculus pieces is demounted from the second storage portion.

FIGS. 8A and 8B are perspective views illustrating the calculus removing device 50 of the fifth embodiment. FIG. 8A illustrates a cylinder 51 in a state in which the inner cylinder 51M is stored in the outer cylinder 51N. FIG. 8B illustrates the cylinder 51 in a state in which the inner cylinder 51M in which the plurality of calculi K are retained is demounted or removed from the outer cylinder 51N.

The cylinder 51 includes the internal cylinder 51M and the outer cylinder 51N. The inner cylinder 51M stores or holds (collects) the calculi K. The inner cylinder 51M possesses a cylindrical shape and the proximal end of the inner cylinder 51M opposing an opening 51Mb (open end of the inner cylinder 51M) is blocked. On the proximal end of the inner cylinder 51M opposing the opening 51Mb, a thread of a screw portion 51Mc to be screwed into a screw groove of a screw portion 51Ne of the outer cylinder 51N is formed so as to project along the axial direction. The inner cylinder 51M is provided with a gripping portion 51Md configured to be gripped with fingertips when separating the inner cylinder 51M from the outer cylinder 51N at the opening 51Mb.

The outer cylinder 51N stores or holds (receives) the inner cylinder 51M so that the inner cylinder 51M is mountable and demountable (removable) from the outer cylinder 51N. A distal end of the inner cylinder 51M projects slightly from (distally beyond) a distal end of the outer cylinder 51N. The outer cylinder 51N possesses a cylindrical shape, and the proximal end of the outer cylinder 51M facing an opening 51Nb of the outer cylinder is blocked or closed. An inner diameter of the outer cylinder 51N corresponds to an outer diameter of the inner cylinder 51M.

When mounting the inner cylinder 51M in the outer cylinder 51N, the inner cylinder 51M is rotated clockwise while pressing the thread of the screw portion 51Mc of the inner cylinder 51M into the screw groove of the screw portion 51Ne of the outer cylinder 51N, so that the thread of the screw portion 51Mc of the inner cylinder 51M is screwed into the screw groove of the screw portion 51Ne of the outer cylinder 51N. In the case where the inner cylinder 51M is demounted or removed from the outer cylinder 51N, the inner cylinder 51M is rotated counterclockwise, and separates the thread of the screw portion 51Mc of the inner cylinder 51M from the screw groove of the screw portion 51Ne of the outer cylinder 51N. The inner cylinder 51M and the outer cylinder 51N may be joined/separated by a fitting engagement between a projection and a depression instead of a screw portion.

The calculus removing device 50 may have a configuration in which the screw 12 provided in the interior of the inner cylinder 51M rotates in the same manner as the first embodiment. In such a case, when the inner cylinder 51M is mounted in the outer cylinder 51N, the proximal side of the screw 12 fits into the rotating member 13B. The calculus removing device 50 may have a configuration in which the screw is joined to the inner peripheral surface of the internal cylinder 51M and the internal cylinder 51M to which the screw is joined is rotated as in the third embodiment. In such a case, when mounting the inner cylinder 51M in the outer cylinder 51N, the proximal end of the internal cylinder 51M fits into the rotating member 13B.

As described thus far, according the calculus removing device 50 of the fifth embodiment, since the cylinder 51 includes the inner cylinder 51M configured to store or hold the calculi K (the calculi are collected in the inner cylinder 51M) and the outer cylinder 51N configured to store or hold the inner cylinder 51M so as to be demountably mountable and coupled to the operating member 13D, the inner cylinder 51M filled with the calculi K may be demounted or removed (separated) from the outer cylinder 51N and a new (empty) inner cylinder 51M may be mounted to the outer cylinder 51N. Therefore, in the case where a pathological examination is performed with respect to the calculi K and the calculi K are discarded, the handling may be performed simply. In addition, in the case where the plurality of calculi K cannot be collected at once in the cylinder 51, removal of the calculi K may be continued by replacing only the inner cylinder 51M.

Although the inventive calculus removing device disclosed here has been described through a plurality of embodiments, modifications and the like, the invention may be modified within the scope of the attached Claims.

For example, the calculus removing device is not limited to a form in which the calculi K may be removed by introducing the device into the ureter 230, and the calculi K may be removed by introducing the device into other portions in the living body. The interior of the living body corresponds, for example, to the renal pelvis and renal calyx 240.

The detailed description above describes embodiments of a calculus removing device and manner of use representing examples of the inventive calculus removing device and manner of use disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A calculus removing device comprising:
a collecting portion configured to be introduced into a living body, the collecting portion including a storage portion configured to store calculi, an open distal end that is always open and that always communicates with the storage portion, and a closed proximal end;
a helical rotatable portion possessing a proximal-most end and a distal-most end, the helical rotatable portion being arranged in the storage portion and configured to move the calculi toward the closed proximal end of the collecting portion while drawing the calculi into the storage portion via the open distal end in association with a rotation of the helical rotatable portion about an axial center line extending along a longitudinal direction of the rotatable portion, the helical rotatable portion being arranged entirely in the storage portion so that the distal-most end and the proximal-most end of the helical rotatable portion are positioned in the storage portion, throughout the drawing-in of the calculi into the storage portion and the movement of the calculi toward the closed proximal end of the collecting portion;
the helical rotatable portion possessing an outer circumferential dimension that is the same while the collecting portion is introduced into the living body and while the calculi are being drawn into the storage portion; and
a hand-operated unit provided with an operating member for rotating the rotatable portion.

2. The calculus removing device according to claim 1, wherein the rotatable portion includes a helical surface that extends along a wound path at cyclic intervals.

3. The calculus removing device according to claim 2, wherein the rotatable portion is configured in such a manner that intervals between axially adjacent helical surfaces are variable.

4. The calculus removing device according to claim 3, further comprising an adjusting member positioned adjacent to the rotatable portion in an axial direction extending from a proximal end of the storage portion toward the open distal end, the adjusting member being configured to vary the intervals between the axially adjacent helical surfaces by a back and forth movement of the adjusting member in the axial direction.

5. The calculus removing device according to claim 1, wherein the rotatable portion rotates within the storage portion.

6. The calculus removing device according to claim 1, wherein the collection portion includes a cylinder possessing an interior defining the storage portion, and wherein the rotatable portion is integral with the cylinder and rotates together with the cylinder.

7. The calculus removing device according to claim 1, further comprising: a retrieving member including a communicating port communicating with the collecting portion and a retrieving portion configured to receive, via the communicating port, the calculi moving from the open distal end to the proximal end of the collecting portion, and to store the received calculi.

8. The calculus removing device according to claim 7, wherein the retrieving member is removably mounted on the collecting portion.

9. The calculus removing device according to claim 1, wherein the collecting portion includes a first storage portion configured to store the calculus, and a second storage portion configured to receive the first storage portion so that the first storage portion is mountable in and removable from the second storage portion, the second storage portion being coupled to the operating member.

10. A calculus removing device comprising:
a calculus collection housing possessing an outer circumferential dimension configured to be introduced into a ureter in a living body, the calculus collection housing possessing a closed proximal end and an interior configured to receive and store calculus collected from the living body so that the calculus collection housing is removable from the living body with the calculus stored in the interior of the calculus collection housing, the calculus collection housing including an open distal end which opens into the interior of the calculus collection housing and through which the calculus in the living body is introduced into the interior of the calculus collection housing, the open distal end always being open while the calculus collection housing is being introduced into the living body, while the interior is receiving calculus collected from the living body and while the calculus collection housing is being removed from the living body with the calculus stored in the interior of the calculus collection housing;
a rotatable portion possessing a helically extending periphery, the helically extending periphery being located in the interior of the calculus collection housing, the helically extending periphery possessing a proximal-most end and a distal-most end, the rotatable portion being rotatable about an axial center line of the rotatable portion;
an operating member operatively connected to the rotatable portion by way of an elongated rotatable member so that operation of the operating member rotates the rotatable portion, including the helically extending periphery so that the rotating helically extending periphery draws the calculus through the open distal end and into the interior of the calculus collection housing and moves the calculus which has been drawn into the interior of the calculus collection housing toward the proximal end of the calculus collection housing, the elongated rotatable member passing through the closed proximal end of the calculus collection housing;
the helically extending periphery being positioned entirely in the interior of the calculus collection housing so that the distal-most end and the of the proximal-most end of the helically extending periphery are positioned in the interior of the calculus collection housing throughout both the drawing-in of the calculi into the interior of the calculus collection housing and the movement of the calculus toward the proximal end of the calculus collection housing; and
the outer circumferential dimension of the calculus collection housing being the same while the calculus collection housing is introduced into the living body, while the calculus is being drawn through the open distal end and into the interior of the calculus collection housing, and while the calculus collection housing is removed from the living body with the calculus stored in the interior of the calculus collection housing.

11. The calculus removing device according to claim 10, wherein the rotatable portion is a screw located in the interior of the calculus collection housing, the screw being connected to the operating member by a wire.

12. The calculus removing device according to claim 11, further comprising an adjusting member positioned between a proximal end of the screw and the proximal end of the calculus collection housing, the adjusting member being axially movable toward the open distal end and away from the open distal end to apply a force to the screw that varies an axial distance between axially adjacent helical surfaces of the screw.

13. The calculus removing device according to claim 10, wherein the helical rotatable portion is rotatable relative to the calculus collection housing.

14. The calculus removing device according to claim 10, wherein the calculus collection housing includes a cylinder and wherein the helical rotatable portion is integral with the cylinder and rotates together with the cylinder.

15. The calculus removing device according to claim 10, further comprising: a retrieving member including a communicating port communicating with the interior of the calculus collection housing and a retrieving portion configured to receive, via the communicating port, the calculi moving from the open distal end to the proximal end of the calculus collection housing, and to store the received calculi.

16. The calculus removing device according to claim 15, wherein the retrieving member is removably mounted on the calculus collection housing.

17. The calculus removing device according to claim 10, wherein the calculus collection housing is removably positioned in a cylinder so that the calculus collection housing is mountable in and removable from a second storage portion, the second storage portion being coupled to the operating member.

* * * * *